US00RE36253E

United States Patent [19]

DiMeglio

[11] E Patent Number: Re. 36,253

[45] Reissued Date of Patent: Jul. 13, 1999

[54] NAIL OIL COMPOSITION

[75] Inventor: Paul J. DiMeglio, Dumfries, Va.

[73] Assignee: The Dime Corporation, Dumfries, Va.

[21] Appl. No.: 07/665,031

[22] Filed: Mar. 6, 1991

Related U.S. Patent Documents

Reissue of:

[64] Patent No.: 4,810,498
Issued: Mar. 7, 1989
Appl. No.: 06/829,007
Filed: Feb. 13, 1986

[51] Int. Cl.[6] ..... A61K 35/78; A61K 7/04; A61K 31/265

[52] U.S. Cl. ..... 424/195.1; 424/61; 514/512; 514/858

[58] Field of Search ..... 424/195.1, 61; 514/512, 858

[56] References Cited

U.S. PATENT DOCUMENTS

| | | | |
|---|---|---|---|
| 2,197,630 | 4/1940 | Carter | 424/61 |
| 2,768,257 | 10/1956 | Blackburn | 424/61 |
| 2,799,613 | 7/1957 | Biodorn | 424/61 |
| 3,334,126 | 8/1967 | Miyazaki et al. | 558/234 |
| 3,382,151 | 5/1968 | Knudsen | 424/61 |
| 4,049,010 | 9/1977 | Mitchell et al. | 132/73.5 |
| 4,250,164 | 2/1981 | Bernstein | 424/61 |
| 4,267,852 | 5/1981 | Hullinger | 132/73.5 |
| 4,286,609 | 9/1981 | Miller | 132/73.5 |
| 4,324,802 | 4/1982 | Koulbanis et al. | 514/786 |
| 4,438,134 | 3/1984 | McGraw | 514/481 |
| 4,530,828 | 7/1985 | Smith et al. | 424/61 |

OTHER PUBLICATIONS

Chem. Abst 105: 49084f, 1986.

Handbook of Nonprescription Drugs. 6th Am. Pharm. Associ. 1980, p. 382.

"Wider Market for Jojoba Seen", *Happi*, Oct. 1985, p. 90.

*Primary Examiner*—John W. Rollins
*Attorney, Agent, or Firm*—Antonelli, Terry, Stout, & Kraus, LLP

[57] ABSTRACT

A nail oil composition is disclosed consisting essentially of a cosmetic oil containing at least 5% by weight jojoba oil, said cosmetic oil having at least 1% by weight tolnaftate dissolved therein. This composition is effective for treating and preventing fungal infestations in fingernails, particularly sculptured nails.

17 Claims, No Drawings

NAIL OIL COMPOSITION

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a nail oil composition suitable for use as a nail and cuticle conditioner. This invention further relates to a nail oil composition including as essential components jojoba oil and tolnaftate. This invention also relates to a method for making a nail oil composition containing tolnaftate and to the method of conditioning nails using the disclosed composition.

2. Description of Related Art

Various compositions for application to or treatment of nails are known including nail polishes, nail polish removers, nail oil emulsions, and the like. These compositions range from those which are purely cosmetic to those which are primarily medicinal. On the medicinal end of the spectrum, there can be mentioned, for example, U.S. Pat. Nos. 3,382,151; 4,250,164 and 2,799,613.

U.S. Pat. No. 3,382,151 describes an aqueous-based, formaldehyde-containing composition which can be applied to fingernails to strengthen them against cracking and splitting. The patent further discloses that the product possesses aseptic properties, curing some inflammation of the matrix of the nail and killing fungi which occasionally infest nails. U.S. Pat. No. 4,250,164 describes a nail polish composition, which has added thereto an anti-psoriasis effective amount of a topical steroid effective against psoriasis. U.S. Pat. No. 2,799,613 describes the use of dibromo-pentachlorocyclohexane as a topical fungicide and bactericide and also discloses including it as an ingredient of nail polish.

Certain oil-containing compositions have been disclosed as being useful as nail and cuticle conditioners or softeners. U.S. Pat. No. 2,765,257, for example, indicates that sulfonated mineral oil acts as an effective cuticle softener; while sulfonated animal and vegetable oils are not effective. Other prior art e.g., U.S. Pat. No. 4,286,609, has disclosed the soaking of fingertips in a hot, aqueous emulsion of vegetable and animal oils to moisturize, smooth and soften the surface of the nails and the tissue surrounding the nails.

Additionally, applicant has previously produced a nail oil formulated primarily from vegetable oils, and including as one constituent jojoba oil, for conditioning nails in connection with the application of artificial nails and with nail sculpturing.

The use of these nail oil compositions for conditioning nails in combination with the application of artificial nails, nail sculpturing and the like, has created a situation favorable for the growth of fungi in the vicinity of the nails. Treatments using such oil compositions tend to enhance moisture retention in nails, thereby providing an environment favorable for fungal growth. Consequently, the recent growth in the use of nail sculpturing and the use of artificial or false nails has been accompanied by an increase in the incidence of fungal infestations or infections in nails.

Treating such infections with the prior art's aqueous-based formaldehyde-containing composition or the nail polish of the '613 patent is not completely satisfactory. Repeated use of such compositions, while potentially remedying the fungus infection, oftentimes harms the nails or contiguous area of the skin in some other fashion, or for other reasons such compositions simply are not desirable or convenient for the repeated applications typically needed to solve the problem.

Thus, it is an object of the present invention to provide a nail oil composition, which provides a safe and effective remedy for or prevention against fungal infestation or infection in nails, as well as a method for making the nail oil composition and a method for using the nail oil composition.

DESCRIPTION OF THE INVENTION

In a first aspect, the present invention relates to a nail oil composition consisting essentially of a cosmetic oil containing at least 5% by weight jojoba oil, said cosmetic oil having at least 1% by weight tolnaftate dissolved therein.

The invention also relates to a method for treating a fungal infestation or infection in nails, particularly sculptured nails and the like comprising periodically applying to said nails an oil composition consisting essentially of a cosmetic oil containing at least 5% by weight jojoba oil, said cosmetic oil having dissolved therein an antifungal effective amount of tolnaftate. A cosmetic oil composition having dissolved therein at least about 1% by weight tolnaftate preferably is used in a preventative manner to retard the growth and development of fungi in sculptured nails or nails having applied to the surface thereof any artificial member, e.g., a false nail. For treating nails having an involved fungal infection, it is preferred to use a cosmetic oil composition having dissolved therein at least about 3% by weight tolnaftate.

The present invention further relates to a method of making a tolnaftate-containing nail oil composition comprising (a) heating a cosmetic oil containing at least 5% by weight jojoba oil to a temperature of at least about 100° C. so as to form a heated jojoba oil-containing cosmetic oil; and (b) dissolving above at least 1.0% by weight tolnaftate in said heated jojoba oil-containing cosmetic oil.

The present invention is directed to a nail oil composition suitable for preventing or treating fungal infestations or infections in nails. Tolnaftate (chemically known as O-2-naphthyl-m,N-dimethylthio carbanilate), comprises the antifungal constituent of the present invention; its preparation is described in U.S. Pat. No. 3,334,126. Tolnaftate is manufactured by Orion Corporation Ltd. (Fermion), Finland and by Lusochimia S.p.A., Italy and is available, respectively, from S.S.T. Corp, Clifton, N.J. and Vinchem Inc, Chatham, N.J.

Applicant has found quite surprisingly, that while tolnaftate exhibits limited solubility in most oils (e.g., tolnaftate is soluble at 1 part per 100 parts in heart of maize), it can be dissolved with agitation at a significantly higher weight fraction in heated cosmetic oils containing jojoba oil and will not crystallize when the oil is cooled to ambient temperature, i.e., the tolnaftate remains dissolved therein. In particular, at least up to about 50% by weight tolnaftate can be dissolved in pure jojoba oil heated to about 100° C. and the tolnaftate will not crystallize when the oil is cooled to ambient temperature. Similarly, applicant has found that about 25% by weight tolnaftate can be dissolved with agitation in a heated cosmetic oil containing 50% by weight jojoba oil and 50% by weight of a blend of other cosmetic seed oils, e.g., almond oil, safflower oil, rice bran oil and sesame seed oil, and the tolnaftate will not crystallize when the oil is cooled to ambient temperatures. While the jojoba oil can be heated to a higher temperature prior to dissolving the tolnaftate therein, such is not generally desired as it can lead to oxidative discoloration of the oil.

Attempts at dissolving the tolnaftate into other oils, including paraffins, at a concentration of above about 1% by weight has not been successful when jojoba oil is not present as a component of the oil composition. Thus, as far as applicant is aware, in order to obtain a cosmetic oil composition having tolnaftate dissolved therein at a concentration of above 1% by weight, jojoba oil is an essential constituent.

Preferably, to minimize energy requirements, the tolnaftate is dissolved in heated jojoba oil (pure), and the oil solution then is blended with other cosmetic oil constituents in order to prepare a final nail oil composition potentially having a wide range of tolnaftate contents, without causing crystallization of the dissolved tolnaftate. The tolnaftate-containing jojoba oil can be added slowly to other cosmetic oils with continuous stirring. In this way, nail oil compositions containing at least 1% by weight tolnaftate and preferably 3% by weight tolnaftate and above can be formulated economically.

In addition to the jojoba oil, the nail oil composition of the present invention typically includes other cosmetic oils. Generally, oils, principally of vegetable origin, which are used widely in cosmetic products can be used in this invention, although naturally occurring fats and oils of animal origin also can be used on occasion. These cosmetic oils are composed principally of saponifiable esters, principally fatty acid triglycerides. Vegetables oils which can be used in the present invention include soybean oil, avocado oil, corn oil (heart of maize), turnsole oil, sesame oil, safflower oil, almond oil, rice bran oil, olive oil, linseed oil, cottonseed oil, peanut oil, an coconut oil. As animal fats and oils can be mentioned mink oil and beef tallow.

As noted, the jojoba oil comprises at least about 5% and up to about 50% of the cosmetic oil in the formulation, while the other cosmetic oils mentioned above constitute the balance. At concentrations of jojoba oil below about 5%, the nail oil composition does not contain a sufficient amount of tolnaftate to be fully effective against fungal infections, whereas at a concentration of jojoba oil above about 50%, the nail oil composition is prohibitively expensive. Preferably, the jojoba oil comprises at least 15% by weight of the cosmetic oil.

Perfume oils or other cosmetic materials such as protein (Keratin), vitamins, anti-oxidants and the like also may be added as optional ingredients to the nail oil composition of the present invention in small quantities provided that such materials do not in any way jeopardize the effectiveness of tolnaftate as an anti-fungal agent or reduce the solubility of the tolnaftate in the nail oil composition. By describing the composition as "consisting essentially of" said recited components, applicant intends to permit the introduction of such ingredients, in small amounts, which do not change the basic and novel characteristics of the basic nail oil composition.

The cosmetic oil, including as essential constituents at least 5% by weight jojoba oil (preferably at least 15% by weight) and an anti-fungal amount of tolnaftate, preferably is applied daily to nails as a cuticle and nail conditioner. The frequency of application, however, can vary depending upon the concentration of tolnaftate in the composition and the condition of the nails. The composition is particularly effective when applied topically to the nails after sculpturing the nails or after any artificial application has been made to the surface of the nails. The composition can be applied simply by painting a few drops onto the nail and spreading with a small nail brush or by massaging the composition into the nail and cuticle, for example, using one's thumb. Nails also can be soaked in a bath, preferably heated, of the nail oil of this invention. This treatment is especially useful for treating nails already infected with a fungus, such as a mold or mildew.

The following tables illustrate suitable compositions for practicing the present invention and are not intended to limit the scope of the invention which is defined in the appended claims.

TABLE 1

| | |
|---|---|
| Sweet Almond oil | 1.25 parts |
| Safflower oil | 1.25 parts |
| Rice Bran oil | 1.25 parts |
| Sesame Seed oil | 1.25 parts |
| Jojoba oil | 1 part |
| Tolnaftate | 0.06 parts |

TABLE 2

| | |
|---|---|
| Jojoba oil | 50 parts |
| Sesame oil | 12.5 parts |
| Safflower oil | 12.5 parts |
| Almond oil | 12.5 parts |
| Rice Bran oil | 12.5 parts |
| Tolnaftate | 3.1 parts |

The above formulations can be prepared by dissolving with agitation the tolnaftate in the full complement of jojoba oil at a temperature of about 100° C. followed by blending the heated jojoba oil containing the dissolved tolnaftate with the remaining oil components and then cooling (with agitation) the mixture to ambient temperature. Alternatively, the tolnaftate could be dissolved directly into a blend of the cosmetic oils heated to a temperature of about 100° C. followed by cooling as described in the following example.

EXAMPLE

A blend of 50% by weight jojoba oil, 12.5% by weight sesame seed oil, 12.5% by weight safflower oil, 12.5% by weight almond oil and 12.5% by weight rice bran oil was prepared and heated to about 100° C. To this heated blend of oils, it was found that tolnaftate in an amount of 25.2% based on the weight of the oils, could be dissolved with agitation and would not crystallize when the oil is cooled with agitation to ambient conditions.

Although preferred embodiments of the invention have been described above, it will be appreciated that other embodiments are contemplated along with modifications of disclosed features as being within the scope of the invention, which is defined in the appended claims.

I claim:

1. A [nail oil] composition consisting essentially of a cosmetic oil containing at least 5% by weight jojoba oil, said cosmetic oil having at least 1% by weight tolnaftate dissolved therein.

2. The composition of claim 1 contining at least about 3% by weight dissolved tolnaftate.

3. The composition of claim 2 containing at least 15% jojoba oil by weight.

4. The composition of claim 1 containing at least about 50% jojoba oil by weight.

5. The composition of claim 1 wherein said cosmetic oil is a vegetable oil selected from the group consisting of almond oil, safflower oil, rice bran oil, sesame seed oil, and mixtures thereof.

6. A method of treating a fungal infection in nails comprising periodically applying to said nails a nail oil composition consisting essentially of a cosmetic oil containing at least 5% by weight jojoba oil, said cosmetic oil having dissolved therein at least about 3% by weight tolnaftate.

7. The method of claim 6 wherein said nail oil composition contains at least 15% by weight jojoba oil.

8. A method of making a tolnaftate-containing nail oil comprising (a) heating a cosmetic oil containing at least 5% by weight jojoba oil to a temperature of at least about 100° C. to form a heated jojoba oil-containing cosmetic oil; and (b) dissolving above at least 1.0% by weight tolnaftate in said heated jojoba oil-containing cosmetic oil.

9. The method of claim 8 wherein at least 3.0% by weight tolnaftate is dissolved in said heated jojoba oil-containing cosmetic oil.

10. The method of claim 8 wherein said cosmetic oil contains at least 50% by eight jojoba oil and at least 10% by weight tolnaftate is dissolved in said heated jojoba oil-containing cosmetic oil.

11. The method of claim 10 wherein said jojoba-containing cosmetic oil containing said dissolved tolnaftate is slowly blended with a cosmetic oil selected from the group consisting of almond oil, safflower oil, rice bran oil, sesame seed oil, and mixtures thereof.

*12. A method of treating a fungal infection in nails or cuticles comprising periodically applying to said infection an antifungal oil composition consisting essentially of a cosmetic oil containing at least 5% by weight jojoba oil, said cosmetic oil having dissolved therein at least about 3% by weight tolnaftate.*

*13. The method of claim 12 wherein said antifungal oil composition contains at least 15% by weight jojoba oil.*

*14. A method of making a tolnaftate-containing antifungal oil composition comprising:*

*(a) heating a cosmetic oil containing at least 5% by weight jojoba oil to form a heated jojoba oil-containing composition; and*

*(b) dissolving above at least 1% by weight tolnaftate in said heated jojoba oil-containing composition.*

*15. The method of claim 14 wherein at least 3% by weight tolnaftate is dissolved in said heated jojoba oil-containing composition.*

*16. The method of claim 14 wherein said cosmetic oil contains at least 50% by weight jojoba oil and at least 10% by weight tolnaftate is dissolved in said heated jojoba oil-containing composition.*

*17. The method of claim 16 wherein said jojoba-containing composition containing said dissolved tolnaftate is blended with a cosmetic oil selected from the group consisting of almond oil, safflower oil, rice bran oil, sesame oil and mixtures thereof.*

* * * * *